United States Patent [19]

Michel

[11] Patent Number: 4,585,439

[45] Date of Patent: Apr. 29, 1986

[54] PORTABLE INFUSION UNIT

[75] Inventor: Peter Michel, Burgdorf, Switzerland

[73] Assignee: Disetronic AG., Burgdorf, Switzerland

[21] Appl. No.: 648,051

[22] Filed: Sep. 7, 1984

[30] Foreign Application Priority Data

Sep. 7, 1983 [CH] Switzerland ............... 4887/83

[51] Int. Cl.⁴ .................................... A61M 37/00
[52] U.S. Cl. ................................. 604/155; 604/211
[58] Field of Search ............... 604/155, 152, 211, 208, 604/154; 74/89.15, 97

[56] References Cited

U.S. PATENT DOCUMENTS

| | | | |
|---|---|---|---|
| 2,734,504 | 2/1956 | Crescas et al. | 604/155 |
| 3,720,211 | 3/1973 | Kyrias | 604/155 |
| 3,812,843 | 5/1974 | Wootten et al. | 604/155 |
| 4,196,730 | 4/1980 | Wilson | 604/155 |
| 4,351,332 | 9/1982 | Whitney et al. | 604/155 |
| 4,407,659 | 10/1983 | Adam | 604/155 |

Primary Examiner—John D. Yasko
Attorney, Agent, or Firm—Brady, O'Boyle & Gates

[57] ABSTRACT

A driver sleeve (8) is pivoted in the casing (1) of the unit which is driven by a motor controlled by a control device and supplied by a battery. A threaded rod (11) forming the piston rod of an injection ampule (15) is placed into the driver sleeve (8) in a non-rotary but longitudinally shiftable fashion. A nut (21) provided with an external toothing (20) is rigidly held on the rear end of the injection ampule (15) in the casing (1). A connecting part (27) provided with a catheter (32) receives the outlet piece (30) of the injection ampule (15) and is screwed to the casing (1) so that the exchangeable injection ampule (15) is completely surrounded by the casing (1) and the connecting part (27) and the outlet piece (30), resting close to the connecting part (27), of the injection ampule (15) communicates with the catheter (32). The threaded rod (11) is placed into the piston (14) of the injection ampule (15) with the nut (21) being screwed on and is placed into the casing (1) together with the injection ampule (15). When the driver sleeve (8) is driven, it moves, with the advancing of the piston (14), through the nut (21) held tightly in the casing (1) adjacent to the rear end of the injection ampule. The unit guarantees a reliable advance of the piston rod even with a low torque of the driving device and has only a length as required by the injection ampule and the necessary piston rod length.

10 Claims, 6 Drawing Figures

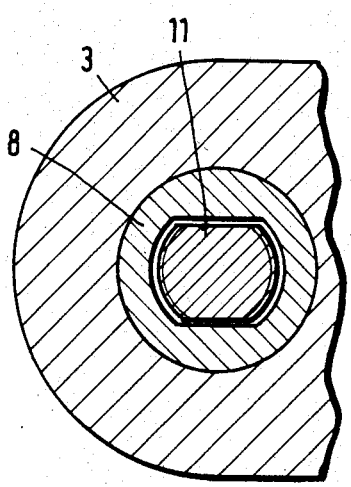
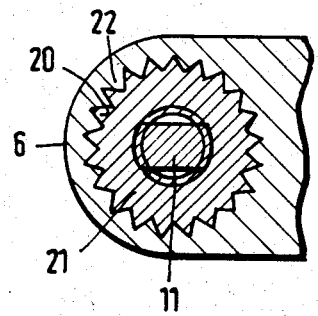
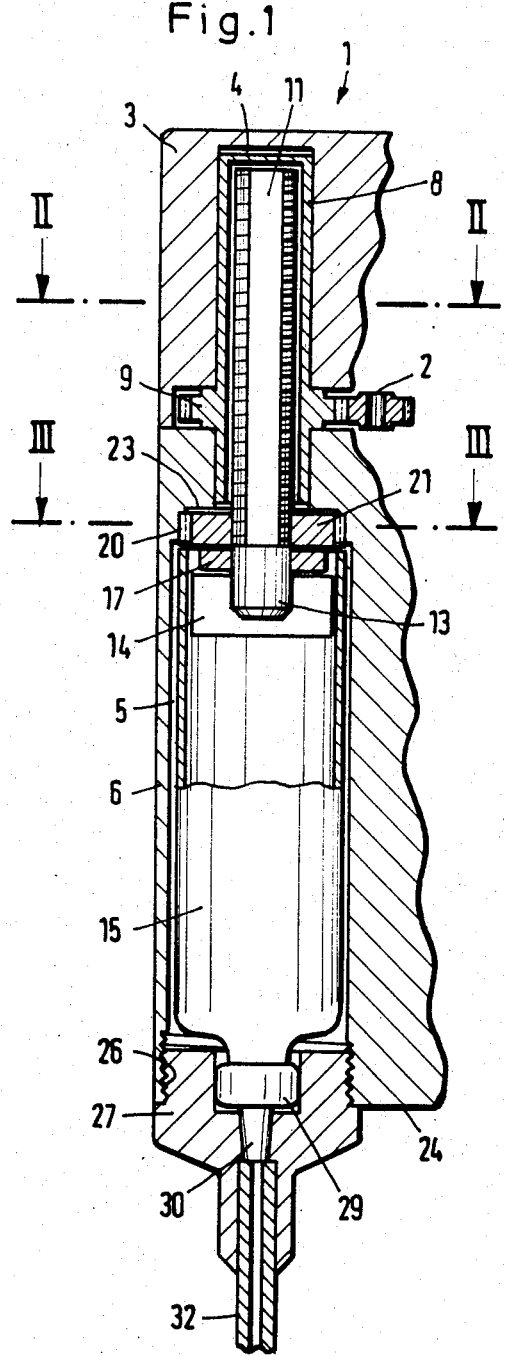

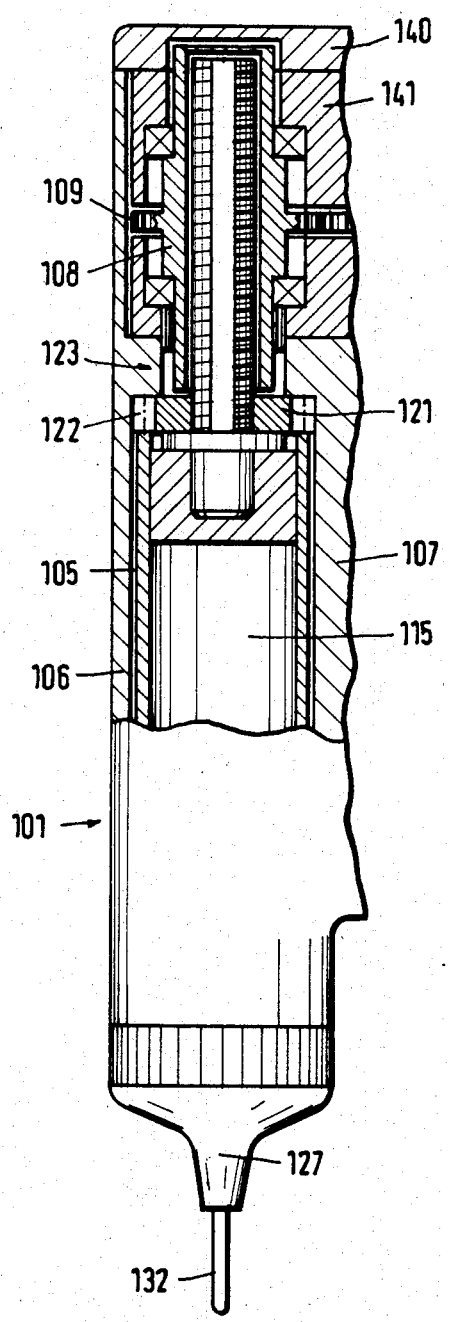
Fig. 4
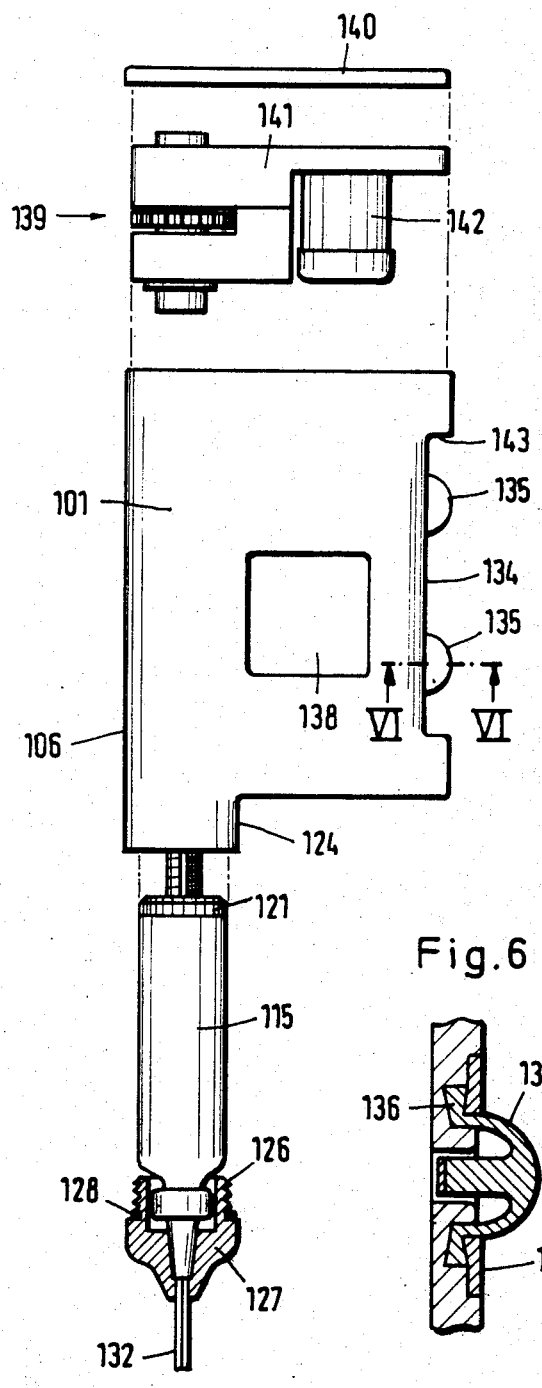
Fig. 5
Fig. 6

PORTABLE INFUSION UNIT

BACKGROUND OF THE INVENTION

The invention concerns a portable infusion unit for the automatic discharge of liquid from an exchangeable injection ampule.

Injection ampules are destined, in contrast to customary ampules, for use as a syringe and, for this purpose, they are provided with a tightly closing piston on one end and open for the introduction of a piston rod and are equipped with an outlet piece on the other end. Injection ampules are also called "carpules".

An infusion unit of this kind is known from the published European Patent Application No. 42 282. The injection ampules to be used with the known unit have a flange at the rear end which is placed into grooves on opposite casing walls of the unit. The piston rod inserted in the piston of the injection ampule is placed on a pinion of the driving device arranged on the bottom of the casing between the walls located opposite each other and is pressed on the pinion by means of a pressing-down element so that it can advance the piston rod which consists of plastic and is smooth in longitudinal direction. In comparison with other units of this kind, for example, the one known from the U.S. Pat. No. 3,886,928, where a gear rack is arranged in the casing which is driven by a pinion of the driving device and is to be connected to the piston rod, the unit has the advantage that the connecting operation is eliminated and, therefore, the unit equipped with the injection ampule is shorter. The disadvantage which exists already in principle with regard to the known units of this kind, i.e. the fact that a high torque is required for the advance of the rod and the risk is run that the rod is not reliably advanced or even runs back owing to the comparatively high counter-pressure, exists even to a higher degree in the case of the unit known from the European Patent Application: Since the pinion does not engage in a gear rack but in a smooth rack, there is the additional risk of slippage whereby the rack may even slide back over the pinion.

SUMMARY OF THE INVENTION

The invention is based on the task of creating a simple unit of the kind mentioned in the introduction whose length, together with the exchangeably inserted injection ampule, is as short as possible and which guarantees a reliable advance of the piston rod.

The structural arrangement of parts in the infusion unit accomplish additionally the task of arranging the injection ampule in the casing so that it is protected against damage, of permitting a water-tight design of the unit and of connecting a catheter to the outlet piece in such a way that it is secured against being pulled away.

BRIEF DESCRIPTION OF THE DRAWINGS

Exemplified embodiments of the invention are further explained below with the help of the drawing. There are shown:

FIG. 1 an axial longitudinal cross-section through a portable infusion unit with inserted injection ampule;

FIG. 2 a cross-section according to line II—II in FIG. 1 in an enlarged scale;

FIG. 3 a cross-section according to line III—III in FIG. 1;

FIG. 4 an axial longitudinal cross-section through an alternative of the infusion unit according to FIG. 1;

FIG. 5 a broken-down representation of the infusion unit according to FIG. 4 in a reduced scale and FIG. 6 a cross-section according to line VI—VI in FIG. 5 in an enlarged scale.

DESCRIPTION OF THE PREFERRED EMBODIMENT

The unit shown in FIGS. 1 to 3 has a casing 1 in which a driving device is arranged. The (not shown) driving device has a stepping motor, operated by a battery and controlled by a control device, which drives a pinion 2. The control device can set the pulse frequency of the control pulses controlling the stepping motor in the course of the day in accordance with a function of the time of the clock determined by the physician and there is a clock and a storage in which certain infusion rates, established by the physician, are stored as control values for certain times, for example, each hour of the day. A control device fulfilling this function is described in the Swiss Patent Application No. 6 559/83.

The rear (in the drawing upper) part 3 of the casing 1 has a cylindrical cavity 4 whose rear end is closed and whose front end ends in a cylindrical cavity 5, coaxial to it, of the front (in the drawing lower) part 6 of the casing 1 whose cavity wall forms a mounting support for an exchangeable injection ampule and a nut as is described in greater detail further below. A driver sleeve 8 is pivoted in the cavity 4 on which a toothed rim 9 is formed which engages in the pinion 2 and runs in a recess of the casing part 3 adjusted to the toothed rim 9 whereby the walls of the recess prevent an axial shifting of the toothed rim 9 and thus also of the sleeve 8. In order to be able to insert the sleeve 8 with the toothed rim 9 when producing the unit, the casing 1 consists of two pieces between which the recess is formed and which are joined together, for example, by gluing, after the sleeve 8 is inserted.) A threaded rod 11 is inserted in the driver sleeve 8 which is secured against turning but can be shifted longitudinally. In order to prevent it from turning, the threaded rod 11 is flat on its opposite sides and the borehole of the driver sleeve is correspondingly adjusted in its cross-section. Thus, the threaded rod 11 has two plane, parallel, smooth, longitudinal surfaces, on which it is carried along by the corresponding plane inner wall surfaces of the sleeve 8, and two cylinder jacket segments provided with a thread which are at a distance from the two smooth, cylindrical inner wall surfaces of the sleeve 8. A disk 17 is pivoted on the front end (in the drawing lower end) of the threaded rod 11 which is formed with a threadless peg 13, projecting coaxially to the threaded rod 11, which can be introduced into the blind hole of the piston 14 of an injection ampule 15 which is provided to receive a piston rod. The diameter of the disk 17 is smaller than the diameter of the piston 14 so that the disk, resting on the piston 14, can be introduced into the ampule tube. A nut 21 provided with an external toothing 20 is screwed on the lower part of the threaded rod 11 and adjacent to the disk 17. When placing the threaded rod 11 into the sleeve 8 which is described further below, the external toothing 20 of the nut 21 is made to engage with a corresponding internal toothing 22 on the jacket surface of the inner wall of the casing part 6 adjacent to the rear end wall 23 of the cylindrical cavity 5. The thickness of the nut 21 is greater than the tooth width of the internal toothing 22 and the diameter of the crown line of the external toothing 20 corresponds approximately with the outer diameter of the injection ampule 15 so that the nut 21, after the further below described inserting of the injection ampule 15, is clamped in, secured against axial shifting, between the rear end of the injection ampule 15 and the rear end wall 23 of the cavity 5. The free, front (in the drawing lower) end 24 of the casing part 6 is provided with an internal thread into which a connecting part 27, provided with an external thread, is screwed. The latter has a cylindrical cavity to receive the aluminum cap 29 of the injection ampule 15 and a conical cavity to receive the outlet piece 30 of the injection ampule 15, consisting of plastic, the so-called "Luer". When screwing on the connecting part 27, the outlet piece 30 is pressed tightly against the wall of the conical cavity. A catheter 32, communicating with the conical cavity and formed by a flexible tube, is welded into the front end of the connecting part 27 and is adjacent to the outlet opening of the outlet piece 30, resting tightly against the conical cavity walls, or is located at a short distance from it.

Commercially available injection ampules can be used for the unit. The injection ampule 15 shown in the drawing is such a commercially available injection ampule whose piston has a threaded blind hole for a piston rod. Preferably, injection ampules already filled, for example, with insulin are used which are supplied without piston rod. However, the patient may also use empty injection ampules which are supplied with a commercially available piston rod which can be screwed into the threaded blind hole. After the injection ampule has been filled, the patient must then only screw the piston rod out of the threaded blind hole.

The filled injection ampule 15 is placed into the connecting part 27 with its outlet piece 30—after having removed a protective cap which closes it. Subsequently, the threaded rod 11 on which the nut 21 is placed resting against the disk 17 is inserted into the blind hole of the piston 14 with the peg 13 pivoted on it so that the disk 17 rests against the piston 14. Now, the injection ampule 15 is introduced into the cavity 5 with the help of the non-slip connecting part 27 and moved towards the rear whereby it is led through the cylindrical cavity wall and the threaded rod 11 is guided coaxially towards the driver sleeve 8 and into the latter. When advancing further, the external toothing 20 of the nut 21 engages into the internal toothing 22. (In order to facilitate the introduction of the threaded rod 11 into the driver sleeve 8, the rear end of the threaded rod may be tapered. Accordingly, the external toothing 20 of the nut 21 may be beveled on the front to be introduced into the internal toothing 22). Finally, the connecting part 27 is screwed into the casing end 24 with its thread 26. When being screwed out, the nut 21 resting against the front wall 23 of the cavity 5 pushes forward the disk 17 projecting beyond the end of the injection ampule and, thus, also the piston 14 resting in a flush fashion in the rear end of the injection ampule so that the liquid discharges from the injection ampule 15 into the catheter 32 communicating with the outlet piece 30. The dimensions decisive for the advance of the piston 14 when screwing on the connecting part 27 (length of the cavity 5, of the cavities in the connecting part 27, of the thread 26, etc.) are selected in such a way that the liquid fills, with certainty, the catheter up to the point of the needle connected to it, i.e. a slight liquid flow leaves the needle. After the connecting part 27 has been screwed on, the rear edge of the hollow cylinder of the injection ampule 15 rests against the nut 21 so that the nut is secured against axial shifting between the rear injection ampule edge and the front wall 23.

The unit which is now ready for operation operates as follows:

The motor controlled by the control device drives the toothed rim 9 formed on the driver sleeve 8 with the help of the pinion 2. When turning, the driver sleeve 8 carries along the threaded rod which moves ahead as a screw spindle with the advance of the piston 14 by the nut 21 held in a non-rotary manner in the casing by the toothing 22.

The rotary support of the disk 17 and the peg 13 on the threaded rod 11 has the advantage, in comparison with a rigid support which is, of course, also possible in principle, that no friction occurs on the piston and, therefore, the power consumption of the driving motor is kept low. It has, surprisingly, been demonstrated that this rotary support does not make the introduction of the threaded rod 11 into the driver sleeve 8 (and of the nut toothing 20 into the internal toothing 22) more difficult but, on the contrary, it actually facilitates it in comparison with a rigid support. In case of a rigid support, the connecting part 27 with the injection ampule 15 is to be turned in such a way when introduced that the threaded rod 11 gets into the correct position for the introduction into the driver sleeve 8. In case of the rotary support, a slight jarring motion is sufficient for the threaded rod 11 to slide into the driver sleeve 8.

The alternative of the unit shown in FIGS. 4–6 is, in principle, designed in the same way as the unit of FIGS. 1–3. Therefore, essentially only those parts of the alternative will be explained below in greater detail which differ from the parts of the unit according to FIGS. 1–3. The parts of the alternative which correspond in their functions with the parts 1, 2, 3, ... mentioned in connection with FIGS. 1–3 are given the reference numbers 101, 102, 103 ..., if they are assigned such, in FIGS. 4–6.

The casing 101 of the shown alternative has a hollow cylindrical chamber 105 serving as a mounting support for the injection ampule 115. The chamber walls are formed by the front (in the drawing lower) part of the left, semi-cylindrical lateral wall 106 of the casing 101, a semi-cylindrical partition 107 and a cylindrical casing attachment 124 provided with an internal thread.

The partition 107 extends from the casing attachment 124 to an end wall 123 adjacent to the chamber 105 in the rear (in the drawing on top) which has a hole adjusted to the driver sleeve 108 and which supports the nut 121. The jacket surface of the cylindrical chamber-wall adjacent to the end wall 123 has the internal toothing 122. In front (in the drawing at the bottom), the chamber 105 can be closed off by means of a connecting part 127, screwable into the casing attachment 124, to which a catheter 132 is rigidly connected which has a (not shown) second attachment part at the other end for the needle. The second attachment part is also rigidly connected with the catheter, for example, welded to it, and is provided with a thread into which a threaded socket, rigidly connected with a needle, can be screwed. In this way, a connection of the needle via the catheter to the connecting part of the injection ampule is guaranteed which is secured against traction. An O ring 128 is provided on the threaded socket 126 of the connecting part 127 so as to secure a water-tight connection of the connecting part 127 with the casing attachment 124.

A (not shown) control device is arranged in the space between the partition 107 and the right lateral wall 134 of the casing 101 for the driving device. The control device has two circuit contacts which can be actuated by exerting pressure on two buttons 135 arranged on the right lateral wall 134 (FIG. 6). The buttons consist of elastic material and have a collar 136 which is pushed to the edge of the passage hole for the actuation of the circuit contact by means of a ring 137 so that the hole is closed off in a water-tight manner. An indication of the control device can be read through a window 138 inserted in the casing wall.

The casing 101 is open on its rear (in the drawing upper) side for the installation of the control device and a component 139 comprising the driver sleeve 108 and the driving device whereby the opening is tightly closed off by a cover 140 after the installation. The component 139 has a support (141) on which the driver sleeve 108 rests in a rotary manner and which carries a stepping motor 142 as well as a gear with a pinion driving the toothed rim 109 of the driver sleeve 108. The component 139 placed into the casing 101 is held between the end wall 123 as well as a casing attachment 143 and the cover 140 whereby the driver sleeve 108 projects into the hole of the end wall 123 and a blind hole in the cover 140. Two separate (not shown) batteries are provided to feed the stepping motor 142 and the control device which are arranged in two small chambers which can be tightly closed by means of screw closures in the front (in FIG. 5 lower) part of the casing 101 between the chamber 105 and the right lateral wall 134.

With the help of the invention, a reliable advancing of the piston is secured even with a slight torque of the driving device (for example, due to a reduced battery voltage) whereby only the axial force necessary for the piston advance acts on the threaded rod forming the piston rod and no radial forces: The solution according to the invention makes it possible to hold the entire injection ampule with its connecting part in the casing in a secure and protected fashion. The casing can surround all parts of the unit in this instance and can be made water-proof so that the patient may take a shower or even a bath without running any risk.

Owing to the rigid connection of the catheter 32 with the connecting part 27, the risk is avoided that the patient tears off the catheter, for example, while sleeping. The unit according to the invention need only be made as long as it is required by the injection ampule and the necessary piston rod length.

I claim:

1. Portable infusion unit for the automatic discharge of liquid from an exchangeable injection ampule (15; 115) with a driving device for the advance of the piston (14) of the injection ampule (15; 115) comprising, a rotatable driver sleeve (8; 108) connected in said unit to be rotatably driven by the driving device, a threaded rod (11) for the advance of the piston (14) of the injection ampule (15; 115) a nut (21; 121) threadably connected on the threaded rod (11), said threaded rod (11) removably insertable into said driver sleeve (8; 108) by simple axial movement, means (22; 122) on said unit engagable with said nut (21; 121) to secure said nut against rotation relative to said unit, a non-rotatable but longitudinally shiftable coupling between said driver sleeve (8; 108) and said threaded rod securing said threaded rod (11) against rotation relative to said driver sleeve (8; 108) but allowing it to rotate relative to said nut (21; 121) upon rotation of said driver sleeve relative to the nut by the driving device, said threaded rod (11) and nut (21; 121) removable as a unit from said driver sleeve and unit when the injection ampule (15; 115) is removed from the unit, and said nut held securely in engagement with said means (22; 122) by the rear end of the injection ampule when the threaded rod (11) and nut (21; 121) and the injection ampule are inserted into the unit.

2. Unit according to claim 1, including a housing (1; 101) surrounding all parts of the unit including a cavity (5; 105) for the injection ampule (15; 115) which has an outlet piece (30) on one end thereof, the cavity having an end opening for the replacement of the injection ampule (15; 115) a detachable connecting part (27; 127) connectable to the housing to close the end opening and by means of which the outlet piece (30) of the injection ampule (15; 115) can be connected to a catheter (32; 132).

3. Unit according to claim 2, in which the catheter (32; 132) is rigidly connected with the connecting part (27; 127) and communicates with a cavity of the connecting part into which the outlet piece (30) of the injection ampule (15; 115) can be introduced.

4. Unit according to claim 1, including a toothed rim (9) is placed or formed on the driver sleeve (8), and a pinion (2) driven by the driving device engaged with said toothed rim (9).

5. Portable infusion unit for the automatic discharge of liquid from an exchangeable injection ampule (15; 115) with a driving device for the advance of the piston (14) of the injection ampule (15; 115) comprising, a rotatable driver sleeve (8; 108) connected to be rotatably driven by the driving device, a threaded rod (11) for the advance of the piston (14) of the injection ampule (15; 115) which is inserted in a non-rotary but longitudinally shiftable manner into said driver sleeve (8; 108), a nut (21; 121) on the threaded rod (11), said unit including a mounting cavity (5; 105) for the injection ampule (15; 115) and the nut (21; 121) into which the injection ampule can be axially introduced, an end wall (23; 123) at the rear end of the cavity having a passage hole for the threaded rod (11), said end wall (23; 123) having means (22; 122) cooperating with a surface (20) of the nut (21; 121) to secure said nut against turning, and the nut (21; 121) is held securely between the end wall (23; 123) and the rear end of the injection ampule (15; 115) against axial shifting when the injection ampule (15; 115) is in place.

6. Unit according to claim 5, in which the circumference of the nut (21; 121) has an external toothing (20) and the means on said end wall of the mounting cavity (5; 105) comprising a corresponding internal toothing (22; 122).

7. Portable infusion unit for the automatic discharge of liquid from an exchangeable injection ampule (15; 115) with a driving device for the advance of the piston (14) of the injection ampule (15; 115) comprising, a rotatable driver sleeve (8; 108) connected to be rotatably driven by the driving device, a threaded rod (11) for the advance of the piston (14) of the injection ampule (15; 115) which is inserted in a non-rotary but longitudinally shiftable manner into said driver sleeve (8; 108), a nut (21; 121) on the threaded rod (11) which is held tightly adjacent to the rear end of the injection ampule with the threaded rod (11) and the injection ampule (15; 115) being inserted into the unit, and a disk (17) pivoted on the front end of the threaded rod (11) which rests against the piston (14) when the injection ampule (15) is in place, whereby the nut engages the unit to prevent rotation thereof.

8. Unit according to claim 7, in which the piston (14) of the injection ampule (15) has a blind hole, and the disk (17) having a peg (13) projecting coaxially forward of the threaded rod (11) and being insertable into the blind hole.

9. Portable infusion unit for the automatic discharge of liquid from an exchangeable injection ampule (15; 115) with a driving device for the advance of the piston (14) of the injection ampule (15; 115) comprising, a rotatable driver sleeve (8; 108) connected to be rotatably driven by the driving device, a threaded rod (11) for the advance of the piston (14) of the injection ampule (15; 115) which is inserted in a non-rotary but longitudinally shiftable manner into said driver sleeve (8; 108), said threaded rod (11) having two plain, parallel, longitudinal surfaces, on which it is carried along by two corresponding plain inner wall surfaces of said driver sleeve (8), a nut (21; 121) on the threaded rod (11) which is held tightly adjacent to the rear end of the injection ampule with the threaded rod (11) and the injection ampule (15; 115) being inserted into the unit, whereby the nut engages the unit to prevent rotation thereof.

10. Portable infusion unit for the automatic discharge of liquid from an exchangeable injection ampule (15; 115) with a driving device for the advance of the piston (14) of the injection ampule (15; 115) comprising, a rotatable driver sleeve (8; 108) connected to be rotatably driven by the driving device, a threaded rod (11) for the advance of the piston (14) of the injection ampule (15; 115) which is inserted in a non-rotary but longitudinally shiftable manner into said driver sleeve (8; 108), a nut (21; 121) on the threaded rod (11), said nut engaging the unit to prevent rotation thereof, said unit including a housing (1; 101) surrounding all parts of the unit including a cavity (5; 105) for the injection ampule (15; 115) which has an outlet piece (30) on one end thereof, the cavity having an end opening for the replacement of the injection ampule (15; 115), a detachable connecting part (27; 127) connectable to the housing to close the end opening, a catheter (32; 132) rigidly connected with said connecting part (27; 127) and communicating with a cavity of the connecting part, the outlet piece (30) of the injection ampule (15; 115) being conically tapered towards the front, the cavity of the connecting part (27; 127) being correspondingly conically tapered to receive the outlet piece (30), to connect the same to the catheter (32; 132), and a screw thread connection (26; 126) between the connecting part and the housing (1, 24; 101, 124) so that with the injection ampule (15; 115) and treaded rod (11) with the nut (21; 121) being inserted into the unit, the wall of the cavity in the connecting part (27; 127) is tightly pressed against the outlet piece (30) of the injection ampule (15; 115) with the opposite rear end of the injection ampule held tightly against the nut (21; 121).

* * * * *